United States Patent
Price et al.

(10) Patent No.: US 12,303,473 B1
(45) Date of Patent: *May 20, 2025

(54) THERAPEUTIC METHODS USING BUPROPION HYDROBROMIDE TO TREAT MAJOR DEPRESSIVE DISORDER

(71) Applicants: Richard Louis Price, Suffern, NY (US); Maxwell Zachary Price, Suffern, NY (US)

(72) Inventors: Richard Louis Price, Suffern, NY (US); Maxwell Zachary Price, Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/894,811

(22) Filed: Sep. 24, 2024

Related U.S. Application Data

(63) Continuation of application No. 18/804,196, filed on Aug. 14, 2024, which is a continuation of application No. 18/404,706, filed on Jan. 4, 2024, now Pat. No. 12,083,080.

(60) Provisional application No. 63/605,614, filed on Dec. 4, 2023.

(51) Int. Cl.
*A61K 31/137* (2006.01)
*A61K 31/135* (2006.01)
*A61P 25/24* (2006.01)

(52) U.S. Cl.
CPC .......... *A61K 31/137* (2013.01); *A61K 31/135* (2013.01); *A61P 25/24* (2018.01)

(58) Field of Classification Search
CPC .............................. A61K 31/135; A61P 25/24
See application file for complete search history.

(56) References Cited

U.S. PATENT DOCUMENTS

| | | | |
|---|---|---|---|
| 7,537,784 B2 | 5/2009 | Oberegger et al. | |
| 7,569,610 B2* | 8/2009 | Oberegger | A61P 43/00 514/649 |
| 7,671,094 B2 | 3/2010 | Williams et al. | |
| 11,197,839 B2 | 12/2021 | Tabuteau | |
| 2008/0075774 A1 | 3/2008 | Williams | |

OTHER PUBLICATIONS

Cleveland Clinic, "Treatment-Resistant Depression", https://my.clevelandclinic.org/health/diseases/24991-treatment-resistant-depression, last reviewed on May 16, 2023. (Year: 2023).*
Khan et al., Buproprion Hydrochloride; Profiles of Drug Substances, Excipients and Related Methodology, 41, 2016, 1-30.*
Aplenzin Package Insert, https://www.accessdata.fda.gov/drugsatfda_docs/label/2008/022108lbl.pdf.
Price, M. Z., et al., Extended-Release of Bupropion Hydrobromide (Aplenzin®) Compared to Bupropion Hydrochloride in Treatment Resistant Major Depressive Disorder, J Dep Anxiety, Published: Apr. 27, 2023, pp. 1-3, vol. 12 Iss. 1 No. 1000501.
Shakil, S., et al., Behavioral and Neuronal Effects of Inhaled Bromine Gas: Oxidative Brain Stem Damage, Int. J. Mol. Sci. 2021, 22, 6316.
Marshall et al., "Bupropion and sertraline combination treatment in refractory depression", J. Psychopharm., 9(3), pp. 284-286 (Year: 1995).
Lam et al., "Citalopram and Bupropion-SR: Combining Versus Switching in Patients with Treatment-Resistant Depression", J. Clin. Psych., 65:3, pp. 337-340 (Year: 2004).
Katz, "Bupropion Treatment of Refractory Depression", J. Clin. Psychopharm., 7(1), pp. 51-52 (Year: 1987).
Drugs.com, "Bupropion Dosage", https://www.drugs.com/dosage/bupropion.html#:-:text= Bupropion%20hydrobromide%2017 4 % 20mg%20oral,appropriate%20dose%20for%20such%2otreatment, last updated on Aug. 3, 2023 (Year: 2023).

* cited by examiner

*Primary Examiner* — Kyle A Purdy
(74) *Attorney, Agent, or Firm* — David B. Gornish; Eckert Seamans Cherin & Mellott LLC

(57) ABSTRACT

Disclosed are methods of treating a patient having Major Depressive Disorder (MDD). The methods include administering to the patient a therapeutically effective amount of bupropion hydrobromide in extended-release form. The methods are more therapeutically effective in treating MDD than administration of an equivalent plasma dose of bupropion hydrochloride in extended-release form. Optionally, in addition, the therapeutically effective amount of bupropion hydrobromide reduces the incidence of one or more adverse events (anxiety, agitation and/or insomnia), when compared to the administration of the equivalent plasma dose of bupropion hydrochloride in extended-release form.

12 Claims, 1 Drawing Sheet

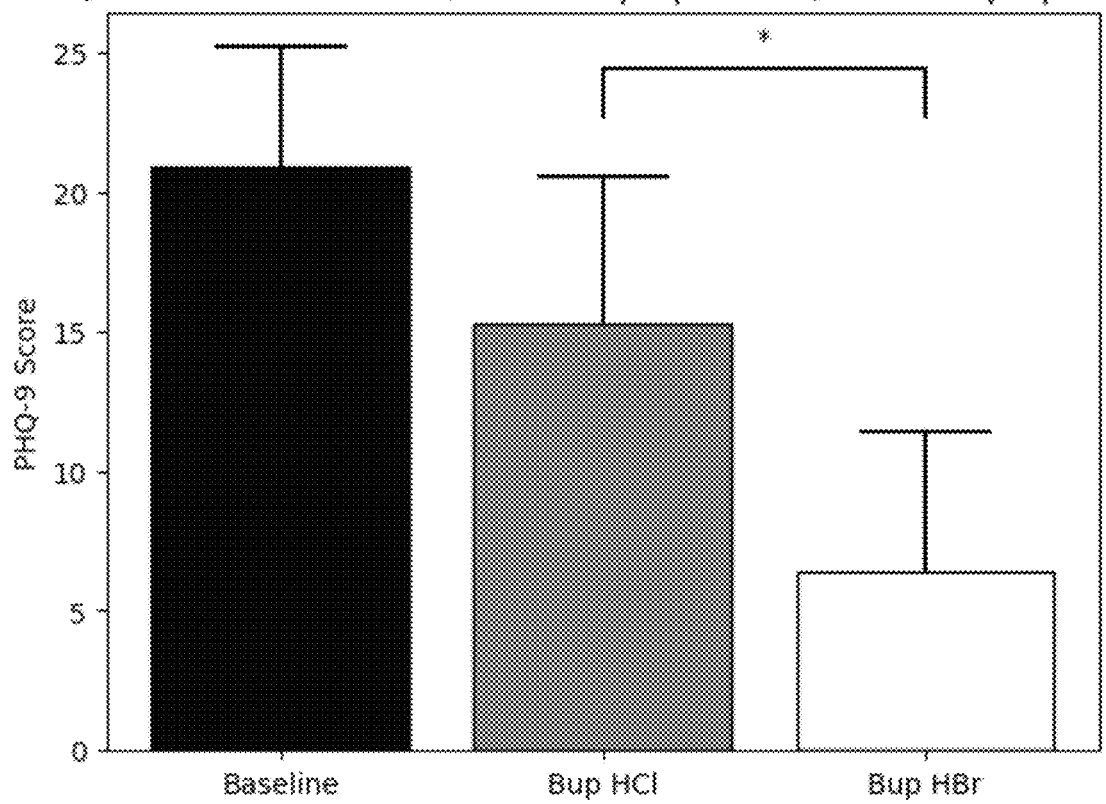

THERAPEUTIC METHODS USING BUPROPION HYDROBROMIDE TO TREAT MAJOR DEPRESSIVE DISORDER

CROSS-REFERENCE TO RELATED APPLICATIONS

This application is a continuation application of U.S. application Ser. No. 18/804,196, filed Aug. 14, 2024 and entitled THERAPEUTIC METHODS USING BUPROPION HYDROBROMIDE, which is a continuation application of U.S. application Ser. No. 18/404,706, filed Jan. 4, 2024, entitled "THERAPEUTIC METHODS USING BUPROPION HYDROBROMIDE", now U.S. Pat. No. 12,083,080, which claims priority to U.S. Provisional Patent Application No. 63/605,614, entitled "Therapeutic Methods Using Bupropion Hydrobromide," filed on Dec. 4, 2023, each of which is incorporated by reference herein in its entirety.

FIELD

The presently disclosed concept relates generally to treatment of depression conditions and potentially other psychiatric disorders using bupropion hydrobromide. The disclosed concept is based on Applicants' novel and surprising finding that bupropion hydrobromide has demonstrated improved clinical efficacy in Major Depressive Disorder (MDD) and Treatment Resistant Depression (TRD), with lower side effects, compared to bupropion hydrochloride.

BACKGROUND

Bupropion is known as an antidepressant of the aminoketone class, chemically unrelated to tricyclics, tetracyclics, selective serotonin reuptake inhibitors (SSRIs), or other known antidepressant agents. The drug resembles a psychostimulant in terms of its neurochemical and behavioral profiles in-vivo, but it does not reliably produce stimulant-like effects in humans at clinically prescribed doses. Its structure closely resembles that of diethylpropion and it is related to phenylethylamines. In its hydrochloride salt form, it is designated as (±)-1-(3-chlorophenyl)-2-[(1,1-dimethylethyl)amino]-1-propanone hydrochloride and by its generic name amfebutamone hydrochloride. Bupropion hydrochloride is commercially available as an immediate release form a sustained release form and an extended-release form (Wellbutrin® XL).

The neurochemical mechanism of the antidepressant effect of bupropion is not well known. Bupropion affects chemicals within the brain that nerves use to send messages to each other. These chemical messengers are called neurotransmitters. The neurotransmitters that are released by nerves are taken up again by the nerves that release them for reuse (this is referred to as reuptake). Many in the field believe that depression is caused by an imbalance among the amounts of neurotransmitters that are released. Bupropion is a selective catecholamine (dopamine and norepinephrine) reuptake inhibitor and works by inhibiting the reuptake of the neurotransmitters dopamine and norepinephrine, an action which results in more dopamine and norepinephrine made available to transmit messages to other nerves. The bupropion molecule itself appears to have a small effect, if any, on the serotonin reuptake mechanism. Accordingly, bupropion is unique in that its major effect is on dopamine, an effect which is not shared by the selective serotonin reuptake inhibitors (SSRIs), e.g. paroxetine (Paxil®), fluoxetine (Prozac®) and sertraline (Zoloft®) or the tricyclic antidepressants or TCAs, e.g. amitriptyline (Elavil®), imipramine (Tofranil®) and desipramine (NORPRAMIN®).

Wellbutrin® XL, i.e., extended-release bupropion HCL, received FDA approval for Major Depressive Disorder (MDD) in 2003 and for Seasonal Affective Disorder (SAD) in 2006. Extended release (XL) bupropion hydrobromide (HBr) (Aplenzin®) received FDA approval in 2008 for both MDD and SAD following demonstration of pharmacokinetic bioequivalence to XL bupropion HCl. However, no human clinical efficacy trials of XL bupropion HBr have been completed and none comparing it to XL bupropion HCl.

The conventional view in the field, considering the study demonstrating pharmacokinetic bioequivalence between XL bupropion HCl and XL bupropion HBr, is that the drug in these different salt forms would be clinically identical in both efficacy and safety. Such conventional wisdom was recently expressed in the medical literature, for example, as follows: "Aplenzin brand could also be a 1-pill-a-day solution (the 522 mg is equivalent to 450 mg Wellbutrin) but otherwise doesn't offer any real clinical advantage as a different salt (hydrobromide) formulation." Puzantian, Talia and Carlat, Daniel J., *Medication Fact Book for Psychiatric Practice*, $5^{th}$ Ed., p. 34 (Carlat Publishing 2020). This report also notes the comparatively high cost of Aplenzin® (XL bupropion HBr), suggesting that providers would not want to prescribe Aplenzin® over the lower cost Wellbutrin® (XL bupropion HCl), since Aplenzin® purportedly "doesn't offer any real clinical advantage" over Wellbutrin®.

Moreover, there is medical literature suggesting that the Br salt may result in an increase in toxicity. For example, in a study of rats who inhaled bromine gas, the rats exhibited abnormal cage behavior such as head hitting, biting, aggression, hypervigilance and hyperactivity. See Shakil, S.; Juncos, J.; Mariappan, N.; Zafar, I.; Amudhan, A.; Amudhan, A.; Aishah, D.; Siddiqui, S.; Manzoor, S.; Santana, C.; Rumbeiha, W.; Salim, S., Ahman, A; Ahmad, S. Behavioral and Neuronal Effects of Inhaled Bromine Gas: Oxidative Brain Stem Damage, *Int. J. Mol. Sci.* 2021, 22(12), 6316. That study suggested the potential of $Br_2$ as a neurotoxin that induces changes in behavior, neuro-histopathology as well as oxidative and metabolic stress in the brain. The abstract of the study concludes: "Taken together, our results predict brain damage and autonomic dysfunction upon $Br_2$ exposure." See also Shader, Richard I MD-Editor-in-chief, Antidepressants as Hydrobromide Salts—Are They a Cause for Concern?, *Journal of Clinical Psychopharmacology* 29(4):p 317-318, August 2009 (expressing reservations about using the HBr salt form of antidepressants, including bupropion, due to potential side effects such as cognitive dysfunction, irritability and greater potential for toxicity).

Concerns about toxicity of the HBr salt form, the FDA's position that XL bupropion HCl is clinically equivalent to XL bupropion HBr, the conventional belief in the field that there is no clinical difference between the drugs and the comparatively lower price of XL bupropion HCl, are all strong motivations for insurers and clinicians to prescribe the generic and lower cost XL bupropion HCl over XL bupropion HBr. There has been no compelling motivation in the field for prescribers to put their patients on XL bupropion HBr over XL bupropion HCl.

However, there are many patients who do not respond to treatment with Wellbutrin® XL as a monotherapy or adjunctive therapy for depression. Further, many patients experience side effects from the XL bupropion HCl, such as anxiety, agitation and insomnia. This can limit the tolerable dose to patients who may benefit from higher doses of the bupropion molecule, but who cannot take such higher doses due to such dose limiting side effects. As noted above regarding conventional wisdom in the field, if a patient does not successfully respond to treatment with XL bupropion HCl, a clinician in the field would be motivated to move on from the bupropion molecule altogether, since the commercially available HBr form of the molecule is perceived in the field as being clinically equivalent to the HCl form. There is thus a need for treatment of depression in patients who fail to respond to Wellbutrin® XL as a monotherapy or adjunctive therapy.

Further, patients suffering from Treatment Resistant Depression (TRD), i.e., who have tried and failed to respond to at least two antidepressant treatments at adequate doses for an adequate duration in the current episode, have limited options. Spravato® is FDA approved for TRD as an adjunctive therapy to another oral antidepressant medication. However, the drug presents a risk of serious adverse outcomes resulting from sedation, dissociation, respiratory depression/arrest and suicidal thoughts/behaviors. It also carries a potential for abuse and misuse. Therefore, Spravato® is only available through a restricted distribution system, under a Risk Evaluation and Mitigation Strategy (REMS). Given these serious risks, patients are permitted to take the drug only under medical supervision and must be monitored by a health care provider for at least two hours after receiving their Spravato® dose. Patients may need to receive the drug up to twice per week. The potential dangers associated with Spravato® and the inconvenience of having to take the medication under medical supervision, gives rise to a strong need for a more convenient and safer treatment for TRD.

The only other pharmacological treatment currently FDA approved for TRD is olanzapine/fluoxetine combination, which is marketed as Symbiax®. Unlike Spravato®, Symbiax® may be administered at home to a patient without medical supervision at the time of administration. However, Symbiax® also carries the risk of serious side effects including sedation, extrapyramidal symptoms, weight gain, and diabetes due to the olanzapine component.

There is thus a strong need in the field for a safe, effective and convenient pharmacological treatment for patients suffering from TRD. There is also a strong need for a safe and effective treatment for patients suffering from MDD and/or TRD who have failed on Wellbutrin® XL.

SUMMARY

Accordingly, in an optional aspect, the disclosed concept is directed to a method of treating a patient having Major Depressive Disorder (MDD) or Treatment Resistant Depression (TRD). The method includes administering to the patient a therapeutically effective amount of bupropion hydrobromide in extended-release form. The patient had previously tried bupropion hydrochloride in extended-release form and experienced an inadequate therapeutic response and/or side effects on an equivalent plasma dose of bupropion hydrochloride in extended-release form for an adequate duration. The method is more therapeutically effective in treating MDD or TRD than administration of an equivalent plasma dose of bupropion hydrochloride in extended-release form, and/or the therapeutically effective amount of bupropion hydrobromide reduces the incidence of one or more adverse events, including at least one of anxiety, agitation and insomnia, when compared to the administration of the equivalent plasma dose of bupropion hydrochloride in extended-release form.

In another optional aspect, the disclosed concept is directed to a method of treating a patient having MDD or TRD. The method includes administering to the patient a therapeutically effective amount of bupropion hydrobromide in extended-release form. The method is more therapeutically effective in treating MDD or TRD than administration of an equivalent plasma dose of bupropion hydrochloride in extended-release form and/or the therapeutically effective amount of bupropion hydrobromide reduces the incidence of one or more adverse events, including at least one of anxiety, agitation and insomnia, when compared to the administration of the equivalent plasma dose of bupropion hydrochloride in extended-release form.

In another optional aspect, the disclosed concept is directed to a method of treating a patient having Treatment Resistant Depression (TRD). The method includes selecting a TRD patient who previously tried bupropion hydrochloride in extended-release form at an adequate plasma dose for an adequate duration in a current depressive episode and experienced an inadequate therapeutic response. The method also includes administering to the patient a therapeutically effective amount of bupropion hydrobromide in extended-release form. The bupropion hydrobromide in extended-release form is more therapeutically effective in treating TRD in the patient than administration of an equivalent plasma dose of bupropion hydrochloride in extended-release form.

In another optional aspect, the disclosed concept is directed to a method of treating a patient having Treatment Resistant Depression (TRD). The method includes selecting a TRD patient who previously tried bupropion hydrochloride in extended-release form at a therapeutic plasma dose, but had to discontinue the bupropion hydrochloride in extended-release form due to side effects. The method also includes administering to the patient a therapeutically effective amount of bupropion hydrobromide in extended-release form. The effective amount of bupropion hydrobromide in extended-release form reduces or ameliorates one or more side effects selected from the group consisting of anxiety, agitation and insomnia, compared to administration of an equivalent plasma dose of bupropion hydrochloride in extended-release form.

In another optional aspect, the disclosed concept is directed to a method of treating a patient having Treatment Resistant Depression (TRD). The method includes selecting a TRD patient that previously tried bupropion hydrochloride in extended-release form at an adequate plasma dose for an adequate duration in a current depressive episode and experienced an inadequate therapeutic response and side effects. The method also includes administering to the patient a therapeutically effective amount of bupropion hydrobromide in extended-release form. The bupropion hydrobromide in extended-release form is more therapeutically effective in treating TRD than administration of an equivalent plasma dose of bupropion hydrochloride in extended-release form when compared to administration of the equivalent plasma dose of bupropion hydrochloride in extended-release form. Also, the therapeutically effective amount of bupropion hydrobromide reduces or ameliorates one or more side effects selected from the group consisting of anxiety, agitation and insomnia, when compared to administration of the equivalent plasma dose of bupropion hydrochloride in extended-release form.

Optionally, in any embodiment, the therapeutically effective amount of bupropion hydrobromide in extended-release form is 174 mg of bupropion hydrobromide and the equivalent plasma dose of bupropion hydrochloride in extended-release form is 150 mg of bupropion hydrochloride.

Optionally, in any embodiment, the therapeutically effective amount of bupropion hydrobromide in extended-release form is 348 mg of bupropion hydrobromide and the equivalent plasma dose of bupropion hydrochloride in extended-release form is 300 mg of bupropion hydrochloride.

Optionally, in any embodiment, the therapeutically effective amount of bupropion hydrobromide in extended-release form is 522 mg of bupropion hydrobromide and the equivalent plasma dose of bupropion hydrochloride in extended-release form is 450 mg of bupropion hydrochloride.

Optionally, in any embodiment, the therapeutically effective amount of bupropion hydrobromide in extended-release form is from 50 mg to 1,200 mg, optionally from 100 mg to 1,000 mg, optionally from 150 mg to 800 mg of bupropion hydrobromide and the equivalent plasma dose of bupropion hydrochloride in extended-release form is from 84 to 88%, optionally about 86.2% of the dose of the therapeutically effective amount of bupropion hydrobromide.

Optionally, in any embodiment, the therapeutically effective amount of bupropion hydrobromide is provided as a monotherapy.

Optionally, in any embodiment, the method is adjunctive to administration of a second drug to treat the patient, optionally adjunctive to another antidepressant, such as an SSRI (selective serotonin reuptake inhibitor) or SNRI (serotonin and norepinephrine reuptake inhibitor).

Optionally, in any embodiment, any of the methods disclosed herein may be practiced on adult or pediatric patients.

Optionally, in any embodiment, the method involves selecting a MDD and/or TRD patient who previously tried and failed on XL bupropion hydrochloride and administering to that patient XL bupropion hydrobromide, wherein the XL bupropion hydrobromide successfully treats the patient's MDD and/or TRD (i.e. with improved efficacy and/or reduced or ameliorated side effects).

Optionally, in any embodiment, safety and efficacy of a drug is assessed at least in part on the basis of a patient's PHQ-9 scores.

Optionally, the method may utilize bupropion HBr in its immediate release (e.g., administered three times daily), sustained release (e.g., administered twice daily) or extended release (e.g., administered once daily) forms.

BRIEF DESCRIPTION OF THE DRAWINGS

The following detailed description of the presently disclosed technology will be better understood when read in conjunction with the appended drawings. In the drawings:

FIG. 1 is a graph comparing mean PHQ-9 (a validated Depression rating scale) scores prior to treatment (Baseline) on XL Bupropion HCl (Bup HCl), and 2 weeks on XL Bupropion HBr (Bup HBr), as described in Example 1, below. Note: *p<0.00001.

DETAILED DESCRIPTION

While therapies, pharmaceutical dosage forms and therapeutic methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Any headings used herein are for organizational purposes only and are not meant to limit the scope of the description or the claims. As used herein, the word "may" is used in a permissive sense (i.e., meaning having the potential to) rather than the mandatory sense (i.e., meaning must). Unless specifically set forth herein, the terms "a," "an" and "the" are not limited to one element but instead should be read as meaning "at least one." The terminology includes the words noted above, derivatives thereof and words of similar import.

As used herein, "and/or" means that either or both of the items separated by such terminology are involved. For example, the phrase "A and/or B" would mean A alone, B alone, or both A and B.

As used herein, "generally" means "in a general manner" relevant to the term being modified as would be understood by one of ordinary skill in the art.

As used herein, the terms "fail," "failure" or "failed," (and other forms of the same) with reference to therapy using a drug (e.g., "the patient failed on Wellbutrin®"), means: (a) that the patient did not respond or did not respond sufficiently (partial but not full therapeutic response); or (b) could not tolerate the drug or tolerate a higher effective dose of the drug due to side effects.

As used herein, the terms "succeed," "succeeded" or "success" (and other forms of the same) with reference to therapy using a drug (e.g., "the patient succeeded on Aplenzin®"), means: (a) that the patient experienced a meaningful therapeutic response; and (b) could tolerate the drug without experiencing significant side effects.

As used herein, the term "Wellbutrin®" or bupropion HCl (or synonymous terms) refer to the drug in its extended-release (XL) once-per-day dosage form, unless, in a given instance, it says explicitly otherwise.

As used herein, the term "Aplenzin®" or bupropion HBr (or synonymous terms) refer to the drug in its extended-release (XL) once-per-day dosage form, unless, in a given instance, it says explicitly otherwise.

As used herein, the term "plasma dose" means the dose of a drug that generates a given peak plasma concentration and pharmacokinetic area under the curve of a drug and/or its metabolites in a patient.

As used herein, the term "equivalent plasma dose" means the dose of a drug that results in an equivalent peak plasma concentration and pharmacokinetic area under the curve of the drug and/or its metabolites to that of another drug. For example, the Pharmacokinetics section (12.3) of the Aplenzin® package insert states: "In a study comparing 10-day dosing with APLENZIN 348 mg once-daily and bupropion HCl extended-release 300 mg once-daily, (following a 3-day titration with bupropion HCl extended-release 150 mg once-daily), APLENZIN peak plasma concentration and area under the curve for bupropion and the 3 metabolites (hydroxybupropion, threohydrobupropion, and erythrohydrobupropion) were equivalent to bupropion HCl extended-release 300 mg, with the average being 8 to 14% lower." Thus, according to this example, 348 mg of XL bupropion HBr is an "equivalent plasma dose" to 300 mg of XL bupropion HCl according to FDA standards and as is to be understood herein.

As used herein, the term "episode" with reference to a consolidated time period in which a patient meets Criteria A-C of DSM-5-TR definition of Major Depressive Disorder (MDD) (as defined below), is a time period of at least two weeks.

As used herein, the phrase "adequate dose" means an amount of a drug that is generally known in the field to have a therapeutic effect in patients. As used herein, the phrase "adequate duration" means the amount of time (usually in days or weeks) that is generally known in the field to be needed for a therapeutic effect to be seen in patients. Thus, for example, if a drug is administered to a patient "at an adequate dose and for an adequate duration," it means that if the patient fails on the drug, a clinician may reasonably conclude that it is not due to inadequate dosing or time on the drug.

Embodiments described herein as "comprising" one or more features may also be considered as disclosure of the corresponding embodiments "consisting of" and/or "consisting essentially of" such features.

When a psychiatrist is presented with a patient exhibiting symptoms indicative of anxiety or depression, the psychiatrist must make a diagnosis to formulate a treatment plan. The psychiatrist's nomenclature, i.e., the criteria for psychiatric evaluation and classification, is informed in large part by the Diagnostic and Statistical Manual of Mental Disorders ("DSM"), a periodically revised psychiatric "Bible" published by the American Psychiatric Association. The current version of the DSM is DSM-5-TR, which was published in 2022. Any disorders mentioned herein that are defined in the DSM-5-TR are to be given the meaning set forth in the DSM-5-TR.

The DSM-5-TR definition of Major Depressive Disorder (MDD) is as follows:

A. Five (or more) of the following symptoms have been present during the same two-week period and represent a change from previous functioning; at least one of the symptoms is either (1) depressed mood or (2) loss of interest or pleasure. (NOTE: Do not include symptoms that are clearly attributable to another medical condition):

1) Depressed mood most of the day, nearly every day, as indicated by either subjective report (eg, feels sad, empty, hopeless) or observations made by others (eg, appears tearful). (NOTE: In children and adolescents, can be irritable mood.)
2) Markedly diminished interest or pleasure in all, or almost all, activities most of the day, nearly every day (as indicated by either subjective account or observation).
3) Significant weight loss when not dieting or weight gain (e.g., a change of more than 5% of body weight in a month), or decrease or increase in appetite nearly every day. (NOTE: In children, consider failure to make expected weight gain.)
4) Insomnia or hypersomnia nearly every day.
5) Psychomotor agitation or retardation nearly every day (observable by others, not merely subjective feelings of restlessness or being slowed down).
6) Fatigue or loss of energy nearly every day.
7) Feelings of worthlessness or excessive or inappropriate guilt (which may be delusional) nearly every day (not merely self-reproach or guilt about being sick).
8) Diminished ability to think or concentrate, or indecisiveness, nearly every day (either by their subjective account or as observed by others).
9) Recurrent thoughts of death (not just fear of dying), recurrent suicidal ideation without a specific plan, or a suicide attempt or a specific plan for committing suicide.

B. The symptoms cause clinically significant distress or impairment in social, occupational, or other important areas of functioning.

C. The episode is not attributable to the direct physiological effects of a substance or to another medical condition.

NOTE: Criteria A through C represent a major depressive episode.

NOTE: Responses to a significant loss (eg, bereavement, financial ruin, losses from a natural disaster, a serious medical illness or disability) may include the feelings of intense sadness, rumination about the loss, insomnia, poor appetite, and weight loss noted in Criterion A, which may resemble a depressive episode. Although such symptoms may be understandable or considered appropriate to the loss, the presence of a major depressive episode in addition to the normal response to a significant loss should also be carefully considered. This decision inevitably requires the exercise of clinical judgement based on the individual's history and the cultural norms for the expression of distress in the context of loss.

D. The occurrence of the major depressive episode is not better explained by schizoaffective disorder, schizophrenia, schizophreniform disorder, delusional disorder, or other specified and unspecified schizophrenia spectrum and other psychotic disorders.

E. There has never been a manic or hypomanic episode. NOTE: This exclusion does not apply if all of the manic-like or hypomanic-like episodes are substance-induced or are attributable to the physiological effects of another medical condition.

Not all recognized psychiatric conditions or FDA approved indications are defined in the DSM-5-TR. Consensus in the field and certain indications that the FDA defines in labeling for approved drugs inform clinicians regarding the meaning of conditions that the DSM does not define. The term "Treatment Resistant Depression" or TRD is not defined in the DSM. However, the well-established understanding of TRD, as set forth in the approved label for the drug Spravato® (which is approved for TRD), and the definition of TRD as used herein is: "A psychiatric condition in a patient that meets DSM-5 criteria for Major Depressive Disorder (MDD) and for which in a current depressive episode, the patient had not responded adequately to at least two different antidepressants of adequate dose and duration." Thus, a patient with TRD necessarily has MDD, but not every MDD patient necessarily has TRD. TRD is considered, by its nature/definition, more difficult to treat than MDD and there is a strong industry need for safe and effective solutions for treating TRD.

The disclosed concept relates to novel methods of using compositions comprising a compound of formula I (bupropion hydrobromide):

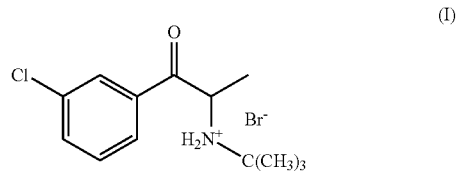 [SMILES: CC([NH2+]C(C)(C)C)C(=O)c1cccc(Cl)c1 ; [Br-]]

(I)

and pharmaceutically acceptable carriers, excipients and/or diluents. These novel therapeutic methods have demonstrated improved efficacy and safety over the HCl version of this molecule.

Optionally, in any embodiment, the bupropion salt can be in the form of its anhydrous, hydrated, and solvated forms, in the form of prodrugs, and in the individually optically active enantiomers of the bupropion salt, such as for example (+)-bupropion and (−)-bupropion. Suitable salts of bupropion also include for example, pharmaceutically acceptable acid addition salts. In certain embodiments, the acid addition salt of bupropion can be indirectly obtained by the separate addition of bupropion and an acid to the core formulation.

Further information regarding the chemistry of bupropion HBr and formulations thereof which may be useful in aspects of treatment according to the disclosed concept, are described in U.S. Pat. No. 7,671,094, which is incorporated by reference herein in its entirety.

It is contemplated that bupropion HBr in any dosage form may be broadly within the scope of the disclosed concept. For example, it may be administered in an immediate release form for therapeutic treatment three times per say. It may be administered in a sustained release form for therapeutic treatment twice per day. However, the preferred dosage form of bupropion HBr is an extended-release (XL) form of bupropion HBr (e.g., currently marketed as Aplenzin®) that may be therapeutically administered to a patient in need thereof once per day.

The disclosed concept is based on insights that Applicants have developed through treatment observations in clinical practice. Contrary to accepted wisdom and expectations in the field, Applicants have surprisingly discovered that XL bupropion HBr has improved efficacy and safety over XL bupropion HCL in treating MDD and TRD. Clinical results demonstrating this phenomenon are described below in Example 1. This is a surprising discovery because skilled persons in the field would have had no reason to believe that XL bupropion HBr would work better clinically in patients suffering from MDD than XL bupropion HCl. All suggestions in the field were to the contrary, particularly given the FDA 505(b)(2) approval of XL bupropion HBr following demonstration of pharmacokinetic bioequivalence to XL bupropion HCl. Nor would skilled persons in the field have reasonably believed that XL bupropion HBr would present a viable alternative in patients with TRD that would work better than XL bupropion HCl. Nor would skilled persons in the field have reasonably believed that XL bupropion HBr would be safer or allow for a higher therapeutic dose in patients who could only tolerate lower plasma doses of XL bupropion HCl. However, Applicants' work in this area has demonstrated that the conventional wisdom on this subject has been incorrect.

It is further noted that according to the Pharmacokinetics section (12.3) of the Aplenzin® package insert, peak plasma concentration and area under the curve for bupropion and its 3 metabolites for patients on once-daily XL bupropion HBr 348 mg (Aplenzin®) were shown, on average, to be 8 to 14% lower than those measurements for patients on once-daily XL bupropion HCl 300 mg. Since the FDA has regarded these drugs as being pharmacokinetically bioequivalent and these doses as being equivalent plasma doses, the hypothetical person of ordinary skill in this field would believe that there are no meaningful clinical differences between these drugs. But the fact that peak plasma concentration and area under the curve for bupropion and its metabolites for patients on Aplenzin® were 8 to 14% lower than those measurements for patients on the HCl version of bupropion, would seem to suggest that if one drug were hypothetically to be more effective, it would the HCl version. Yet, Applicants have discovered the opposite, contrary to conventional wisdom and suggestions in the literature.

Without being limited to any theory, Applicants propose, based on their own findings described in Example 1 (below), that the clinical difference between the two drugs could potentially be explained by one or more (optionally in combination) of the following mechanisms (in no particular order).

Mechanism 1: Blood Brain Barrier (Bromide)

It is possible that the bromine salt component of XL bupropion HBr creates a more acidic environment in and around the brain than does the HCl version of that molecule. This, in turn, may increase permeability of the blood-brain barrier, thus improving brain concentrations of the bupropion compound and/or its active metabolites. Thus, in one optional aspect, the disclosed concept may be directed to a method for increasing permeability of the blood-brain barrier to increase brain concentrations of bupropion and a resulting therapeutic effect to a patient that is treated with bupropion, the method comprising administering to the patient a therapeutically effective amount of XL bupropion HBr. In a related optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which increases permeability of the blood-brain barrier to increase brain concentrations of bupropion, thus providing an improved therapeutic effect to the patient compared to XL bupropion HCl.

Mechanism 2: Hydrobromide Creates Lower pH to Increase Tyrosine Hydroxylase

Tyrosine hydroxylase is an enzyme that is needed to produce the neurotransmitter dopamine. The activity of tyrosine hydroxylase is increased at lower pH. The bromine salt component of XL bupropion HBr creates a more acidic environment than does the HCl version of that molecule. Thus, Applicants propose that the increased activity of tyrosine hydroxylase due to reduced pH from the HBr component increases the amount of dopamine, resulting in an improved therapeutic effect. Moreover, it is possible that the combined effect of increasing the amount of the drug in the brain through increased blood-brain barrier permeability (as set forth above, under Mechanism 1) plus the increase in dopamine, may further explain the improvement in efficacy of the HBr form of bupropion over the HCl form. In an optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which increases activity of tyrosine hydroxylase due to reduced pH from the HBr component, which, in turn, increases the amount of dopamine, thus providing an improved therapeutic effect to the patient compared to XL bupropion HCl.

Mechanism 3: MAO Inhibition—Neurotransmitters Remaining in the Cleft

Serotonin, norepinephrine and dopamine are neurotransmitters that are involved in mitigating depression. Monoamine oxidase (MAO) is an enzyme that removes serotonin, norepinephrine and dopamine from the cleft, which is the space between neurons. Normally, we would want to raise these neurotransmitters in patients suffering from depression; however, MAO will "clean up" these neurotransmitters in the cleft. The effect of this "clean up" is reduction of these neurotransmitters, which could have an adverse effect on a patient's depression symptoms. An acidic environment, however, will tend to inhibit the "clean up" activity of MAO, thereby allowing the neurotransmitters to remain longer and thus provide a positive clinical effect for a person suffering depression. Applicants propose that the bromide salt of XL bupropion may generate a lower pH environment in the patient than the chloride salt of that molecule. This lower pH could inhibit MAO activity and thus contribute to Applicants' clinical observations that XL bupropion HBr is more therapeutically effective than XL bupropion HCl, which does not lower pH as much as the HBr salt. In an optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which inhibits MAO's "clean up" activity due to reduced pH from the HBr component, thus providing an improved therapeutic effect to the patient compared to XL bupropion HCl.

Mechanism 4: Preservation of Dopamine in Presynaptic Vesicle in Acidic Environment The presynaptic terminal is located along the axon of a neuron. It is a compartment where vesicles that contain neurotransmitters, including dopamine, cluster near a region of the plasma membrane. Vesicles release these neurotransmitters during synaptic transmission between neurons. Dopamine is less likely to be degraded in the vesicle in an acidic environment when the dopamine is about to be released during synaptic transmission. As noted above, Applicants contemplate that the bromide salt of XL bupropion generates a lower pH environment in the patient than the chloride salt of bupropion. Therefore, it may be that dopamine is degraded less in the vesicle when a patient takes XL bupropion HBr than when a patient takes XL bupropion HCl. This in turn may cause more dopamine to remain, thereby generating an improved therapeutic effect. In an optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which degrades dopamine less in the vesicle (compared to the HCl salt of bupropion) due to reduced pH from the HBr component, thus providing an improved therapeutic effect to the patient compared to XL bupropion HCl.

Mechanism 5: MAO Inhibition—Preservation of Serotonin (Lower Level of Metabolites)

Tryptophan hydroxylase is the enzyme that makes serotonin. Tryptophan hydroxylase is decreased at lower pHs. It has been found that rats that inhaled bromine gas had decreased levels of the metabolites of serotonin, suggesting that serotonin is not broken down as much, perhaps because the MAO is less active in lower pH environments (as described above). Due to this decreased breakdown, Applicants propose that serotonin is not degraded as quickly and thus provides a patient with an improved anti-depressive effect. In other words, even though bupropion is not known to block serotonin reuptake and increase serotonin levels, the hydrobromide version of the molecule may have an indirect effect on serotonin levels in a patient compared to bupropion HCl due to the more acidic environment which results in inhibition of MAO activity. In other words, the low pH caused by the HBr salt may block the MAO-based degradation pathway of serotonin, thus keeping some serotonin in the patient for longer. In an optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which inhibits the MAO-based degradation pathway due to reduced pH from the HBr component, thereby preserving serotonin in the patient for longer and thus providing an improved therapeutic effect to the patient compared to XL bupropion HCl.

Mechanism 6: Increasing GABA and Mitigating Side Effects

A study of rodents found that bupropion HBr was associated with fewer seizures than bupropion HCl. See Henshall D C, Dürmüller N, White H S, Williams R, Moser P, Dunleavy M, et al., Electroencephalographic and behavioral convulsant effects of hydrobromide and hydrochloride salts of bupropion in conscious rodents. *Neuropsychiatr Dis Treat.* 2009:189-206. The mechanism of action of these anxiolytic and anti-epileptogenic effects can be possibly explained by greater bromide-mediated potentiation of inhibitory potentials through GABA-A receptors (GABA referring to the neurotransmitter gamma-aminobutyric acid). When activated, these receptors increase chloride influx and cause inhibitory neuronal hyperpolarization, which was found to be greater in the presence of bromide than chloride. See Suzuki S, Kawakami K, Nakamura F, Nishimura S, Yagi K, Seino M. Bromide, in the therapeutic concentration, enhances GABA-activated currents in cultured neurons of rat cerebral cortex. *Epilepsy Res.* 1994; 19(2):89-97. Increasing GABA can, for example, reduce seizures, and improve sleep, anxiety and agitation in a patent. Applicants propose that this mechanism may be a contributing factor to the reduced side effects and improved therapeutic outcomes that Applicants observed in patients with MDD and TRD taking XL bupropion HBr compared to XL bupropion HCl. In an optional aspect, the disclosed concept may be directed to selecting a patient that previously tried XL bupropion HCl and had experienced an inadequate therapeutic response and/or side effects. The method further includes administering to that patient a therapeutically effective amount of XL bupropion HBr, which increases GABA in the patient, thus providing an improved therapeutic effect and/or reduced side effects to the patient compared to XL bupropion HCl.

Other Potential Indications

As mentioned above and as will be elaborated upon below in Applicants' study described in Example 1, Applicants have surprisingly discovered that XL bupropion HBr has improved efficacy and safety over XL bupropion HCl in treating Major Depressive Disorder and Treatment Resistant Depression. This was determined in a study of Applicant's patients who were assessed, in part, based on their answers to questions in the Patient Health Questionnaire-9 (PHQ-9) scale (range 0-27). The PHQ-9 is a standardized rating scale used to assess the severity of a patient's depression. The scale considers nine symptoms associated with various forms of depression and asks the patient to rate each of those nine symptoms over the patient's past two weeks on a scale of 0 to 3, where 0=not at all, 1=several days, 2=more than half of the days and 3=nearly every day. The associated symptoms set forth in the PHQ-9 scale are enumerated as follows: (1) Little interest or pleasure in doing things (i.e., anhedonia); (2) Feeling down, depressed, or hopeless; (3) Trouble falling or staying asleep, or sleeping too much; (4) Feeling tired or having little energy; (5) Poor appetite or overeating; (6) Feeling bad about yourself—or that you are a failure or have let yourself or your family down; (7) Trouble concentrating on things, such as reading the newspaper or watching television; (8) Moving or speaking so slowly that other people could have noticed?Or the opposite—being so fidgety or restless that you have been moving around a lot more than usual; and (9) Thoughts that you would be better off dead or of hurting yourself in some way. Scores of 0-4 indicate no depression. Scores of 5-9 indicate mild depression. Scores of 10-14 indicate moderate depression. Scores of 15-19 indicate moderately severe depression. Scores of 20-27 indicate severe depression.

Notably, all patients in the study of Example 1 answered PHQ-9 questions (1), (3), (4), (5) and (7) as improving by at least one point on XL bupropion HBr compared to when they were on XL bupropion HCl. These findings suggest that XL bupropion HBr may be effective and superior to XL bupropion HCl for other disorders that include overlapping symptomology with symptoms set forth in the PHQ-9 questions.

Regarding PHQ-9 question (1), the at least one-point across-the-board improvement in that symptom suggests that XL bupropion HBr may be effective and superior to XL bupropion HCl for treating anhedonia.

PHQ-9 question (3) overlaps with many sleep disorders, such as idiopathic hypersomnia, shift work sleep disorder, narcolepsy and sleep apnea with excessive daytime sleepiness. The at least one-point improvement in the symptom of question (3) suggests that XL bupropion HBr may be effective and superior to XL bupropion HCl for treating any of these sleep disorders.

PHQ-9 question (4) overlaps with symptoms for the recently recognized disorder of COVID brain fog. The at least one-point across-the-board improvement in the symptom of question (4) suggests that XL bupropion HBr may be effective and superior to XL bupropion HCl for treating COVID brain fog.

PHQ-9 question (5) overlaps with symptoms for binge eating disorder and obesity. The at least one-point across-the-board improvement in the symptom of question (4) suggests that XL bupropion HBr may be effective and superior to XL bupropion HCl for treating binge eating disorder and obesity.

PHQ-9 question (7) overlaps with symptoms for Attention Deficit Hyperactivity Disorder (ADHD), COVID brain fog and cognitive disorders such as dementia. The at least one-point across-the-board improvement in the symptom of question (7) suggests that XL bupropion HBr may be effective and superior to XL bupropion HCl for treating ADHD, COVID brain fog and dementia.

In sum, the PHQ-9 questionnaire alludes to certain conditions having overlapping symptomology with depression. A skilled person, based on the data showing superiority of XL bupropion HBr over XL bupropion HCl in treating MDD and TRD (see Example 1) and the fact that all patients experienced at least a one-point improvement in PHQ-9 symptom questions (1), (3), (4), (5) and (7), the skilled person would reasonably infer that XL bupropion HBr could be superior to XL bupropion HCl in other conditions characterized by such symptoms.

Applicants further submit that XL bupropion HBr could be superior to XL bupropion HCl in treating sexual arousal disorder in women or men. XL bupropion HBr could also be superior to XL bupropion HCl in treating smoking cessation.

Applicants further submit that XL bupropion HBr could be superior to XL bupropion HCl (in efficacy and/or side effects) in various depressive disorders, whether as a monotherapy or adjunctive therapy. For example, in addition to being superior for MDD and TRD, Applicants suggest that XL bupropion HBr may be superior to XL bupropion HCl in treating seasonal affective disorder (SAD), postpartum depression and persistent depressive disorder.

EXAMPLES

Aspects of the disclosed concept are further explained by the following examples which should not be construed by way of limiting the scope of the disclosed concept.

Example 1

Comparison of XL Bupropion HBr to Bupropion HCl for MDD in 30 Patients

This study is based on Applicants' recently published study entitled Price M Z, Price R L (2023) Extended-Release of Bupropion Hydrobromide (Aplenzin®) Compared to Bupropion Hydrochloride in Treatment Resistant Major Depressive Disorder. *J Dep Anxiety.* 12:501, which is hereby incorporated by reference herein in its entirety.

In the regular course of Applicants' general outpatient psychiatry practice, Applicants see many patients who suffer from Major Depressive Disorder (MDD) and may not have responded to two or more oral antidepressant medications. Applicants routinely administer the brief and commonly used Patient Health Questionnaire-9 (PHQ-9) scale before starting a new treatment, two weeks after starting treatment to measure initial response, and periodically thereafter. Once-daily, extended-release (XL) bupropion hydrochloride (HCl), sold as Wellbutrin®, a norepinephrine and dopamine reuptake inhibitor, is among the many antidepressants Applicants commonly use because it is available as a generic, does not require insurance prior authorization, and does not typically cause the sexual dysfunction, fatigue, affective flattening, and/or weight gain commonly associated with serotonin reuptake inhibitors. Oftentimes, patients do not adequately respond to generic XL bupropion HCl either because of lack of efficacy or side effects, such as anxiety, agitation, or insomnia.

One treatment strategy Applicants have used successfully is switching patients from generic XL bupropion HCl to an equivalent dose of once-daily, branded XL bupropion hydrobromide (HBr), sold as Aplenzin®, which Applicants have noticed further improves patients' mood with more favorable tolerability. Once-daily, XL bupropion HCl received FDA approval for the treatment of MDD in 2003 and for Seasonal Affective Disorder (SAD) in 2006. Once-daily, XL bupropion HBr (Aplenzin®) received FDA approval in 2008 for both MDD and SAD through the 505(b)(2) pathway following demonstration of pharmacokinetic bioequivalence to XL bupropion HCl. Compared to XL bupropion HCl, XL bupropion HBr was found to produce lower peak plasma concentrations and area under of the curve for both bupropion and its 3 active metabolites (hydroxybupropion, threohydrobupropion, and erythrohydrobupropion). Hence, higher dose plasma equivalents of XL bupropion HBr 174 mg, 348 mg, and 522 mg correspond respectively to XL bupropion HCl 150 mg, 300 mg, and 450 mg.

However, prior to Applicants' study, no human clinical efficacy trials of XL bupropion HBr have been completed and to date there have been no head-to-head studies comparing it to generic XL bupropion HCl.

Bromide salts have been used in the past in humans to treat seizures, anxiety, and insomnia, three potentially limiting side effects of taking XL bupropion HCl. A study of rodents found that bupropion HBr was associated with fewer seizures than bupropion HCl. While not being limited to this theory, the mechanism of action of these anxiolytic and anti-epileptogenic effects can be possibly explained by greater bromide-mediated potentiation of inhibitory potentials through GABA-A receptors. When activated, these receptors increase chloride influx and cause inhibitory neuronal hyperpolarization, which was found to be greater in the presence of bromide than chloride. Recent renewed interest around bupropion has been spurred by the 2022 FDA approval of a combination of shorter-acting, low dose bupropion HCl (105 mg) and high dose dextromethorphan HBr (45 mg) administered twice daily for non-treatment resistant Major Depressive Disorder in adults. Presently, the only FDA-approved oral medication for adult Treatment-Resistant Depression (TRD), defined as failing two or more antidepressants of adequate dose and duration in the current episode, is the combination of fluoxetine and olanzapine, which carries side effects of sedation, extrapyramidal symptoms, weight gain, and diabetes due to the olanzapine component. Applicants wanted to compare equivalent FDA-approved dosing of once-daily XL bupropion HBr to once-daily generic XL bupropion HCl in patients with TRD to measure antidepressant efficacy and tolerability.

The following study protocol was approved by the WCG-IRB institutional ethics committee and conducted in accordance with principles set forth in the Helsinki Declaration. Applicants obtained informed consent from each patient prior to conducting a retrospective chart review on 30 adult patients with TRD (18 females, 12 males) who directly switched from their maximally tolerated dose of generic XL bupropion HCl, due to inadequate response and/or side effects, to an equivalent dose of XL bupropion HBr, open-label, in the regular course of Applicants' general outpatient psychiatry practice. The Patient Health Questionnaire-9 (PHQ-9) scale (range 0-27) was administered prior to starting treatment, after completing a trial of XL bupropion HCl, and after 2 weeks on XL bupropion HBr. The PHQ-9 is a reliable and valid clinical and research tool that measures functionality and depression severity, whereby scores of 5, 10, 15, and 20 correspond to mild, moderate, moderately severe, and severe depression and a 5-point change is considered clinically meaningful. Statistical analysis was performed using a within-subject, 2-tailed t-test with a significance level of $p<0.05$.

Patients had a mean age of 38.7±14.7 years, had failed a mean of 4±2 antidepressants, and had a mean baseline PHQ-9 score of 20.9±4.3 prior to taking a mean XL bupropion HCl dose of 300 mg/day (range 150-450 mg/day) for a mean duration of 88.8 weeks (range 4-480 weeks). After 2 weeks on a mean XL bupropion HBr dose of 348 mg/day (range 174-522 mg/day), these patients demonstrated a decrease in PHQ-9 scores from a mean of 15.3±5.3 on XL bupropion HCl to a mean of 6.4±5.0 on XL bupropion HBr ($t=-8.63$, $p<0.00001$). The most commonly encountered side effects with XL bupropion HCl were insomnia (21 patients), anxiety (19 patients), and gastrointestinal upset (2 patients), which resolved on XL bupropion HBr except for some residual insomnia (3 patients). 96.7% of patients (29 of 30) chose to continue on XL bupropion HBr rather than change back to XL bupropion HCl. The one patient who chose not to continue on XL bupropion HBr described it as "too powerful" and "too stimulating" compared to XL bupropion HCl, even at the lowest available dose of 174 mg. FIG. 1 shows mean PHQ-9 scores prior to treatment (Baseline) on XL Bupropion HCl (Bup HCl), and 2 weeks on XL Bupropion HBr (Bup HBr)—note $p<0.00001$.

This study found that adult patients with severe TRD experienced rapid and significantly improved mood with greater tolerability on XL bupropion HBr compared to generic XL bupropion HCl. Greater tolerability also affords capacity to increase XL bupropion HBr to its maximally approved dose, which is not always possible on XL bupropion HCl due to treatment-emergent side effects, such as insomnia, anxiety, and gastrointestinal upset. Based on mean PHQ-9 depression scores, patients improved from depression ratings of "severe" at baseline and "moderately severe" on XL bupropion HCl to "mild" after 2 weeks on XL bupropion HBr. Given that patients had been taking XL bupropion HCl well past the time frame required for it to take effect prior to switching to XL bupropion HBr, it is likely that improvements in PHQ-9 scores were attributable to the switch as all other concurrent treatments were held constant during this transition period. Among the many previously failed antidepressant trials prior to a maximally tolerated dose of XL bupropion HCl, administered before direct switch to XL bupropion HBr, five included the combination of bupropion HCl and dextromethorphan. All five patients in this subgroup preferred once-daily XL bupropion HBr over the combination of XL bupropion HCl plus dextromethorphan due to improved antidepressant efficacy on XL bupropion HBr. Superior efficacy may be explained by the ability to raise the XL bupropion component to 522 mg compared to a fixed, lower dose of XL bupropion 210 mg divided twice daily, and the once daily dosing of XL bupropion HBr that provides consistent antidepressant exposure over a 24-hour period, avoiding BID (twice a day) dose dumping and pharmacokinetic peaks and troughs.

As demonstrated in this study, patients suffering from Treatment-Resistant Depression experienced rapid and significant improvement in mood with greater tolerability when switching from generic XL bupropion HCl to an equivalent dose of XL bupropion HBr (Aplenzin®).

Example 2

Phase M Double-Blind Active Control Treatment Resistant Major Depressive Disorder Study A phase III double-blind study is conducted on a subset of patients having Major Depressive Disorder who also suffer from Treatment Resistant Depression. Exclusion criteria for this study are any patients suffering from seizures, known hypersensitivity to bupropion, eating disorders, schizophrenia or bipolar disorder. Inclusion criteria for this study are adult patients ages 18 through 64 who have taken two oral antidepressants of adequate dose and duration in the current episode of Major Depressive Disorder.

The study includes a total of fifty patients (N=50). Initially, all patients are given a two-week washout from a previous oral antidepressant or are not currently taking an oral antidepressant. The patients are administered once daily bupropion HCl XL 150 mg, which is flexibly dosed to 300 mg by day 4 and 450 mg by day 11, to the extent required for treatment response and/or as tolerated. The treatment is continued for a total of six weeks. After six weeks, there is a five-day bupropion HCl XL washout. Next, the patients are administered once daily bupropion HBr XL 174 mg, which is flexibly dosed to 348 mg by day 4 and 522 mg by day 11, to the extent required for treatment response and/or as tolerated. This part of the study is continued for a total of six weeks.

Measures are assessed based on weekly changes on the Montgomery Asberg Depression Rating Scale (MADRS) from baseline on bupropion HCl compared to bupropion HBr. Also, side effects leading to discontinuation on bupropion HCl compared to bupropion HBr are considered. The primary endpoint of the study is significant change in MADRS by week 6 on bupropion HBr compared to bupropion HCl. A secondary endpoint is statistically significant change in MADRS by week 2 on bupropion HBr compared to bupropion HCl.

In this study, bupropion HBr is shown to be more effective, works faster, and has fewer side effects leading to discontinuation in TRD than bupropion HCl.

Example 3

A similar study to that of Example 2 is also conducted, except that the 50 patients are broken into two arms—one arm of 25 patients taking bupropion HCl XL and the other arm of 25 patients taking bupropion HBr XL. The results are the same as in Example 2.

Exemplary Embodiments

In sum, until Applicants' discovery of the disclosed concept, the skilled artisan would not have reasonably believed that the hydrobromide salt form of bupropion would be superior to the hydrochloride salt form of that molecule. According to conventional wisdom, both were believed to be bioequivalent and if there were any difference, the literature suggested that the hydrobromide salt may be less safe than the hydrochloride. Physicians who tried their patients on a failed course of Wellbutrin® would have had no motivation to switch their patients to the more costly, purportedly bioequivalent and possibly less safe Aplenzin®. Applicants' discovery has unexpectedly demonstrated that this conventional thinking was incorrect.

The following exemplary embodiments further describe optional aspects of the presently disclosed technology and are part of this Detailed Description. These exemplary embodiments are set forth in a format substantially akin to claims (each with numerical designations followed by a capital letter), although they are not technically claims of the present application. The following exemplary embodiments refer to each other in dependent relationships as "embodiments" instead of "claims."

1A. A method of treating a patient having TRD comprising administering to the patient a therapeutically effective amount of bupropion hydrobromide, optionally in extended-release (once per day) form, thereby treating the patient's TRD.

2A. The method of embodiment 1A, wherein the therapeutically effective amount of bupropion hydrobromide is 174 mg, 348 mg or 522 mg of bupropion hydrobromide.

3A. The method of embodiment 1A or 2A, wherein the therapeutically effective amount of bupropion hydrobromide is administered as a monotherapy or adjunctive to administration of a second drug to treat the patient.

4A. The method of any one of embodiments 1A to 2A, wherein the therapeutically effective amount of bupropion hydrobromide is from 50 mg to 1,200 mg, optionally from 100 mg to 1,000 mg, optionally from 150 mg to 800 mg.

1B. A method of treating a patient having MDD or TRD, the method comprising administering to the patient a therapeutically effective amount of bupropion hydrobromide in extended-release form, wherein the patient had previously tried bupropion hydrochloride in extended-release form and experienced an inadequate therapeutic response and/or side effects on an equivalent plasma dose of bupropion hydrochloride in extended-release form for an adequate duration, wherein the method is more therapeutically effective in treating MDD or TRD than administration of an equivalent plasma dose of bupropion hydrochloride in extended-release form, and/or wherein the therapeutically effective amount of bupropion hydrobromide reduces the incidence of one or more adverse events selected from the group consisting of anxiety, agitation and insomnia, when compared to the administration of the equivalent plasma dose of bupropion hydrochloride in extended-release form.

2B. The method of embodiment 1B, wherein:
(a) the therapeutically effective amount of bupropion hydrobromide in extended-release form comprises 174 mg of bupropion hydrobromide and the equivalent plasma dose of bupropion hydrochloride in extended-release form comprises 150 mg of bupropion hydrochloride; or
(b) the therapeutically effective amount of bupropion hydrobromide in extended-release form comprises 348 mg of bupropion hydrobromide and the equivalent plasma dose of bupropion hydrochloride in extended-release form comprises 300 mg of bupropion hydrochloride; or
(c) the therapeutically effective amount of bupropion hydrobromide in extended-release form comprises 522 mg of bupropion hydrobromide and the equivalent plasma dose of bupropion hydrochloride in extended-release form comprises 450 mg of bupropion hydrochloride.

3B. The method of embodiment 1B or 2B, wherein the method is adjunctive to administration of a second drug to treat the patient, optionally adjunctive to an SSRI or an SNRI.

4B. The method of any one of embodiments 1B to 3B, wherein the patient was able to tolerate a higher plasma dose of bupropion hydrobromide in extended-release form than bupropion hydrochloride in extended-release form.

5B. The method of embodiment 4B, wherein the patient failed on 150 mg of extended release bupropion hydrochloride but succeeded on 348 mg or 522 mg of extended release bupropion hydrobromide.

6B. The method of embodiment 4B, wherein the patient failed on 300 mg of extended release bupropion hydrochloride but succeeded on 522 mg of extended release bupropion hydrobromide.

1C. A therapeutic dosage form comprising a combination of bupropion HBr and dextromethorphan HBr in therapeutically effective amounts for once-a-day dosing.

2C. The therapeutic dosage form of embodiment 1C, wherein the dosage form comprises once-a-day extended-release bupropion HBr (174 mg, 348 mg or 522 mg) and once-a-day extended release dextromethorphan HBr (15 mg, 30 mg or 45 mg).

3C. A method of treating a patient having MDD or TRD comprising administering to the patient the therapeutic dosage form of any one of embodiments 1C to 2C.

1D. A method of treating a patient having MDD or TRD, the method comprising administering to the patient a therapeutically effective amount of bupropion hydrobromide in extended-release form, wherein the method is more therapeutically effective in treating MDD or TRD than administration of an equivalent plasma dose of bupropion hydrochloride in extended-release form, and/or wherein the therapeutically effective amount of bupropion hydrobromide reduces the incidence of one or more adverse events selected from the group consisting of anxiety, agitation and insomnia, when compared to the administration of the equivalent plasma dose of bupropion hydrochloride in extended-release form.

2D. The method of embodiment 1D, wherein:
(a) the therapeutically effective amount of bupropion hydrobromide in extended-release form comprises 174 mg of bupropion hydrobromide and the equivalent plasma dose of bupropion hydrochloride in extended-release form comprises 150 mg of bupropion hydrochloride; or
- (b) the therapeutically effective amount of bupropion hydrobromide in extended-release form comprises 348 mg of bupropion hydrobromide and the equivalent plasma dose of bupropion hydrochloride in extended-release form comprises 300 mg of bupropion hydrochloride; or
- (c) the therapeutically effective amount of bupropion hydrobromide in extended-release form comprises 522 mg of bupropion hydrobromide and the equivalent plasma dose of bupropion hydrochloride in extended-release form comprises 450 mg of bupropion hydrochloride.

3D. The method of embodiment 1D or 2D, wherein the method is adjunctive to administration of a second drug to treat the patient, optionally adjunctive to another antidepressant, such as an SSRI or SNRI.

1E. A method of treating a patient having any disorder selected from the group consisting of: anhedonia, idiopathic hypersomnia, shift work sleep disorder, narcolepsy and sleep apnea with excessive daytime sleepiness, COVID brain fog, ADHD, dementia, sexual arousal disorder, smoking cessation, seasonal affective disorder, postpartum depression, persistent depressive disorder, depression in bipolar disorder, premenstrual dysphoric disorder, binge eating disorder and chronic weight management in obese adults, the method comprising administering to the patient a therapeutically effective amount of bupropion hydrobromide in extended-release form, wherein the method is more therapeutically effective in treating any one of the aforementioned disorders than administration of an equivalent plasma dose of bupropion hydrochloride in extended-release form, and/or wherein the therapeutically effective amount of bupropion hydrobromide reduces the incidence of one or more adverse events selected from the group consisting of anxiety, agitation and insomnia, when compared to the administration of the equivalent plasma dose of bupropion hydrochloride in extended-release form.

2E. The method of embodiment 1E, wherein the method is adjunctive to administration of a second drug to treat the patient.

1F. A method of treating a patient having any disorder selected from the group consisting of: anhedonia, idiopathic hypersomnia, shift work sleep disorder, narcolepsy and sleep apnea with excessive daytime sleepiness, COVID brain fog, ADHD, dementia, sexual arousal disorder, smoking cessation, seasonal affective disorder, postpartum depression, persistent depressive disorder, depression in bipolar disorder, premenstrual dysphoric disorder, binge eating disorder and chronic weight management in obese adults, the method comprising administering to the patient a therapeutically effective amount of bupropion hydrobromide in extended-release form, wherein the patient had previously tried bupropion hydrochloride in extended-release form and experienced an inadequate therapeutic response and/or side effects on an equivalent plasma dose of bupropion hydrochloride in extended-release form for an adequate duration, wherein the method is more therapeutically effective in treating any one of the aforementioned disorders than administration of an equivalent plasma dose of bupropion hydrochloride in extended-release form, and/or wherein the therapeutically effective amount of bupropion hydrobromide reduces the incidence of one or more adverse events selected from the group consisting of anxiety, agitation and insomnia, when compared to the administration of the equivalent plasma dose of bupropion hydrochloride in extended-release form.

2F. The method of embodiment 1F, wherein the method is adjunctive to administration of a second drug to treat the patient.

1G. A method of treating a patient having MDD and/or TRD, the method comprising:
selecting a MDD and/or TRD patient who previously tried bupropion hydrochloride in extended-release form at an adequate plasma dose for an adequate duration in a current depressive episode and experienced an inadequate therapeutic response; and
administering to the patient a therapeutically effective amount of bupropion hydrobromide in extended-release form, wherein the bupropion hydrobromide in extended-release form is more therapeutically effective in treating MDD and/or TRD in the patient than administration of an equivalent plasma dose of bupropion hydrochloride in extended-release form.

1H. A method of treating a patient having MDD or TRD, the method comprising:
selecting a MDD and/or TRD patient who previously tried bupropion hydrochloride in extended-release form at a therapeutic plasma dose, but had to discontinue the bupropion hydrochloride in extended-release form due to side effects; and
administering to the patient a therapeutically effective amount of bupropion hydrobromide in extended-release form, wherein the effective amount of bupropion hydrobromide in extended-release form reduces or ameliorates one or more side effects selected from the group consisting of anxiety, agitation and insomnia, compared to administration of an equivalent plasma dose of bupropion hydrochloride in extended-release form.

1I. A method of treating a patient having MDD and/or TRD, the method comprising:
selecting a MDD and/or TRD patient that previously tried bupropion hydrochloride in extended-release form at an adequate plasma dose for an adequate duration in a current depressive episode and experienced an inadequate therapeutic response and side effects; and
administering to the patient a therapeutically effective amount of bupropion hydrobromide in extended-release form, wherein the bupropion hydrobromide in extended-release form is more therapeutically effective in treating MDD and/or TRD than administration of an equivalent plasma dose of bupropion hydrochloride in extended-release form when compared to administration of the equivalent plasma dose of bupropion hydrochloride in extended-release form, and wherein the therapeutically effective amount of bupropion hydrobromide reduces or ameliorates one or more side effects selected from the group consisting of anxiety, agitation and insomnia, when compared to administration of the equivalent plasma dose of bupropion hydrochloride in extended-release form.

As described herein, the disclosed concept demonstrates that the hydrobromide salt of bupropion can surprisingly be a treatment option for MDD and/or TRD patients who: (a) had taken the hydrochloride salt of bupropion and experienced inadequate (or no) therapeutic response; (b) had to discontinue bupropion HCl due to side effects; or (c) who tolerated bupropion HCl to an extent and perhaps received some clinical benefit from it, but wanted an option with greater efficacy and/or reduced side effects.

While the presently disclosed technology has been described in detail and with reference to specific examples thereof, it will be apparent to one skilled in the art that various changes and modifications can be made therein without departing from the spirit and scope thereof. It is understood, therefore, that the presently disclosed technology is not limited to the particular embodiments disclosed, but it is intended to cover modifications within the spirit and scope of the present presently disclosed technology.

What is claimed is:

1. A method of treating a patient having Major Depressive Disorder (MDD), the method comprising:
selecting a MDD patient who previously tried bupropion hydrochloride in extended-release form at an adequate plasma dose for an adequate duration in a current depressive episode and experienced an inadequate therapeutic response; and
administering to the patient a therapeutically effective amount of bupropion hydrobromide in extended-release form, wherein the bupropion hydrobromide in extended-release form is more therapeutically effective in treating MDD in the patient than administration of an equivalent plasma dose of bupropion hydrochloride in extended-release form.

2. The method of claim 1, wherein the therapeutically effective amount of bupropion hydrobromide in extended-release form is 174 mg of bupropion hydrobromide and the equivalent plasma dose of bupropion hydrochloride in extended-release form is 150 mg of bupropion hydrochloride.

3. The method of claim 1, wherein the therapeutically effective amount of bupropion hydrobromide in extended-release form is 348 mg of bupropion hydrobromide and the equivalent plasma dose of bupropion hydrochloride in extended-release form is 300 mg of bupropion hydrochloride.

4. The method of claim 1, wherein the therapeutically effective amount of bupropion hydrobromide in extended-release form is 522 mg of bupropion hydrobromide and the equivalent plasma dose of bupropion hydrochloride in extended-release form is 450 mg of bupropion hydrochloride.

5. The method of claim 1, wherein the therapeutically effective amount of bupropion hydrobromide in extended-release form is from 150 mg to 800 mg of bupropion hydrobromide and the equivalent plasma dose of bupropion hydrochloride in extended-release form is from 84 to 88% of the dose of the therapeutically effective amount of bupropion hydrobromide.

6. The method of claim 5, wherein the equivalent plasma dose of bupropion hydrochloride in extended-release form is about 86.2% of the dose of the therapeutically effective amount of bupropion hydrobromide.

7. The method of claim 1, wherein the method is adjunctive to administration of a second drug to treat the patient.

8. The method of claim 1, wherein the patient previously tried and failed at least one selective serotonin reuptake inhibitor (SSRI) or serotonin and norepinephrine reuptake inhibitor (SNRI) that had been administered for adequate dose and duration or that had been discontinued due to side effects.

9. The method of claim 6, wherein the patient who previously tried bupropion hydrochloride in extended-release form experienced one or more side effects selected from the group consisting of anxiety, agitation and insomnia and wherein the one or more side effects were reduced or ameliorated when the patient was administered the therapeutically effective amount of bupropion hydrobromide in extended-release form.

10. A method of treating a patient having Major Depressive Disorder (MDD), the method comprising:
selecting a MDD patient that previously tried bupropion hydrochloride in extended-release form at an adequate plasma dose for an adequate duration in a current depressive episode and experienced an inadequate therapeutic response and side effects; and
administering to the patient a therapeutically effective amount of bupropion hydrobromide in extended-release form, wherein the bupropion hydrobromide in extended-release form is more therapeutically effective in treating MDD than administration of an equivalent plasma dose of bupropion hydrochloride in extended-release form, and wherein the therapeutically effective amount of bupropion hydrobromide reduces or ameliorates one or more side effects selected from the group consisting of anxiety, agitation and insomnia, when compared to administration of the equivalent plasma dose of bupropion hydrochloride in extended-release form.

11. The method of claim 10, wherein the therapeutically effective amount of bupropion hydrobromide in extended-release form is from 150 mg to 800 mg of bupropion hydrobromide and the equivalent plasma dose of bupropion hydrochloride in extended-release form is from 84 to 88% of the dose of the therapeutically effective amount of bupropion hydrobromide.

12. The method of claim 10, wherein the method is adjunctive to administration of a second drug to treat the patient.

* * * * *